(12) United States Patent
Berndt

(10) Patent No.: US 6,544,793 B2
(45) Date of Patent: Apr. 8, 2003

(54) METHOD FOR CALIBRATING A SAMPLE ANALYZER

(75) Inventor: Klaus W. Berndt, Timonium, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 134 days.

(21) Appl. No.: 09/845,071

(22) Filed: Apr. 27, 2001

(65) Prior Publication Data

US 2003/0008401 A1 Jan. 9, 2003

(51) Int. Cl.⁷ .............................................. G01N 21/64
(52) U.S. Cl. ........................... 436/8; 436/63; 436/70; 436/165; 436/172; 356/72; 356/73; 702/19; 702/21
(58) Field of Search ........................... 436/8, 63, 70, 436/164, 165, 172; 356/72, 73, 440, 244, 246; 702/19, 21; 73/1.01, 1.02

(56) References Cited

U.S. PATENT DOCUMENTS

| 5,547,849 | A | * | 8/1996 | Baer et al. | 435/7.24 |
| 6,064,474 | A | * | 5/2000 | Lee et al. | 356/39 |
| 6,127,184 | A | * | 10/2000 | Wardlaw | 436/50 |
| 6,180,314 | B1 | * | 1/2001 | Berndt | 430/180 |
| 6,235,536 | B1 | * | 5/2001 | Wardlaw | 436/172 |
| 6,358,475 | B1 | * | 3/2002 | Berndt | 422/100 |
| 6,359,683 | B1 | * | 3/2002 | Berndt | 356/39 |
| 6,446,020 | B1 | * | 9/2002 | Berndt | 702/104 |
| 6,468,803 | B1 | * | 10/2002 | Berndt | 436/63 |

* cited by examiner

Primary Examiner—Maureen M. Wallenhorst
(74) Attorney, Agent, or Firm—Bruce S. Weintraub

(57) ABSTRACT

The present invention relates to the field of quantitative microspectroscopy, and in particular to a method for calibrating a sample analyzer to obtain a more precise HCT value.

24 Claims, 5 Drawing Sheets

METHOD FOR CALIBRATING A SAMPLE ANALYZER

FIELD OF THE INVENTION

The present invention relates to the field of quantitative microspectroscopy, and in particular to a method for calibrating a sample analyzer.

BACKGROUND OF THE INVENTION

The determination of such blood parameters as the Hematocrit ("HCT"), the Volume of single Red Blood Cells ("RCV"), the Mean Cell Volume ("MCV") and the Red Cell Distribution Width ("RDW") are of eminent clinical interest. Usually, systems based on electrical impedance measurement (Coulter Counter) or based on light scattering (Flow Cytometer) are employed (see. e.g., J. B. Henry, "Clinical diagnosis and management by laboratory methods", W. B. Saunders Company, Philadelphia, 1996, pp. 548 ff. or D. H. Tycko, M. H. Metz, E. A. Epstein, A. Grinbaum, "Flow-cytometric light scattering measurement of red blood cell volume and hemoglobin concentration", Applied Optics 24 (1985), 1355–1365). Impedance counters are complex and expensive instruments that require very careful adjustment and control of instrument and sample parameters. A major disadvantage of flow cytometers is the fact that the parameters of light scattering depend not only on cell volume, but also on the cell's shape.

In 1983, Gray, Hoffman and Hansen proposed a new optical method for determining the volume of cells in a flow cytometer (M. L. Gray, R. A. Hoffman, W. P. Hansen, "A new method for cell volume measurement based on volume exclusion of a fluorescent dye", Cytometry 3 (1983), 428–432). In this method, the cells are suspended in a fluorescent dye, which is unable to penetrate the cell membrane. The level of fluorescence which is produced when a narrow stream of the cell suspension is excited by a focused laser beam will remain constant until a cell arrives in the illuminated region thereby causing a decrease in fluorescence intensity which is directly proportional to the cell's volume. In a flow cytometer, a single cell is passing through the laser-illuminated spot within approximately 10 $\mu$s. Due to this short data acquisition time interval, the electronic detection bandwidth has to be relatively large, which results in a poor signal-to-noise ratio and in a low precision for the volume determination.

The available data acquisition time can be significantly increased by suspending the cells in a stationary sample and applying digital imaging fluorescence microscopy (see P. L. Becker, F. S. Fay, "Cell-volume measurement using the digital imaging fluorescence microscope", Biophysical Journal 49 (1986), A465). In the digital fluorescence microscopy approach, a calibration procedure is required in order to determine the cell volume. Recktenwald and co-workers have introduced a method where the calibration is performed by means of optical transparent and non-fluorescent microspheres that are suspended together with the cells (D. Recktenwald, J. Phi-Wilson, B. Verwer, "Fluorescence quantitation using digital microscopy", Journal Physical Chemistry 97 (1993), 2868–2870). The volume of individual spheres is determined by measuring their projection area under the microscope and transforming this number into a volume, assuming an ideal spherical shape. The decrease in fluorescence intensity as a result of the spheres' volume that is being excluded from emitting fluorescence is used as the required calibration parameter. The advantage of this approach is given by the fact that the calibrating particles are located within the sample itself. In other words, a calibration is performed on the very same sample container, and no extra calibration sample is required.

The use of calibration spheres within a cell suspension is not without problems. First, the introduction of the spheres represents an additional step in the workflow. In systems that are designed for high throughput, this additional step would represent a disadvantage. Secondly, Recktenwald and co-workers observed a tendency of the fluorescent dye molecules to settle down on the sphere's surface, which causes an error. Third, if the optical index of refraction of the spheres does not match well with the liquid's index, then refraction-based artifacts in the measured fluorescence intensity occur at the edges of the spheres. And, finally, the use of microspheres can represent a problem, if e.g. a thin sample thickness in the order of a few micrometers or less is needed.

In order to overcome the problems in the prior art, it has been suggested (U.S. Pat. No. 6,127,184 to Wardlaw) to design a cuvette-like optical sample container for the cell suspension that has different optical pathlengths in different areas. In at least one area, the thickness of the liquid layer of un-diluted blood is so thin (2 to 7 microns) that monolayers of isolated RBCs are formed. In another region, the liquid layer is thicker (7 to 40 microns), and typical chain-like aggregates of RBCs ("Roleaux") are forming. The thick area is used to determine the HCT, and the thin area is used to determine the volume of single red blood cells (RCV). As in the prior art, the blood plasma is stained with a fluorescent dye that is not penetrating into the RBCs.

In a method and apparatus according to Wardlaw, the HCT of the whole blood sample is determined according to the equation $$HCT = \left[1 - \frac{B_a}{B_t}\right] * 100\% \qquad (1)$$

In equation (1), $B_t$ is the fluorescence intensity emerging from an area of known size within a cell-free plasma region. $B_a$ is the fluorescence intensity emerging from another area of same size, but from a region comprising RBCs in Roleaux formation. In practice, $B_t$ is determined by measuring the fluorescence intensity in certain cell-free regions and by extrapolating to a larger size. Interestingly, no height measurement is required for the cuvette in order to determine the HCT.

In equation (1), one has to assume that the photons reemerging from the cuvette are all originating as fluorescence photons within the blood plasma. This is, however, not always the case in practice. There are at least two mechanisms that result in additional photons reemerging from the cuvette that are not generated within the plasma. First, if a plastic cuvette is used, then the plastic material may also emit fluorescence photons. Secondly, all practical dichroic filter units used in fluorescence microscopes show a certain degree of "excitation/emission cross-talk". In other words, a small number of excitation photons will pass through the dichroic filter unit, and will in turn reach the photodetector.

If the number of such non-fluorescence photons is too high, then errors in determining the HCT may occur. Therefore, there is a need for a HCT determination method that would not be affected by fluorescence from a plastic disposable cuvette, or by excitation-emission cross-talk due to imperfect dichroic filter units.

SUMMARY OF THE INVENTION

It is an objective of the present invention to provide a method for calibrating a sample analyzer, and in particular a calibration method for the HCT determination that would not be affected by fluorescence from a plastic disposable cuvette, or by excitation/emission cross-talk due to imperfect dichroic filter units, and that therefore would allow to utilize low-cost plastic disposables as well as imperfect low-cost dichroic filter units.

According to the present invention, the above objective is achieved by depositing a sample of biological fluid, and preferably, whole blood into a chamber, such as for example, an optical cuvette having at least two areas of different thickness, whereby in a preferred embodiment the blood plasma contains a fluorescent dye that does not diffuse into the red blood cells. The sample is illuminated with excitation light so that the plasma emits fluorescence radiation. The fluorescent dye is selected so that neither the excitation light nor the emitted fluorescence light are absorbed by the red blood cells.

The HCT value is determined by:

(a) measuring fluorescence intensity values in cell-free locations within a first area of interest having a size, A, and a first thickness;

(b) extrapolating to the integrated fluorescence intensity, I, from the first area of interest that could be expected under cell-free conditions;

(c) determining the thickness, d, within the first area of interest by utilizing any known method for determining a liquid sample height;

(d) measuring the integrated fluorescence intensity, Icell, in said first area of interest, including all cells in this area;

(e) measuring fluorescence intensity values in cell-free locations within a second area of interest having a size, Acal=A, and a second thickness;

(f) extrapolating to the integrated fluorescence intensity, Ical, from the second area of interest that could be expected under cell-free conditions;

(g) determining the thickness, dcal, within the second area of interest by utilizing any known method for determining a liquid sample height;

(h) using the quantities I, Ical, d, dcal, and A to calculate a calibration constant, C, according to the equation:

$$C = \frac{I - Ical}{(d - dcal) * A}$$

and (i) using the quantities I, Icell, d, C, and A to calculate the HCT value of the sample according to the equation $$HCT = \frac{I - Icell}{C * A * d}.$$

DETAILED DESCRIPTION OF THE INVENTION

According to the method of the present invention, a sample of a biological fluid, such as preferably, blood and more preferably, undiluted blood that contains suspended red blood cells (RBCs) is deposited into a chamber, such as for example, an optical cuvette having at least two areas of different thicknesses. Preferably, the cuvette is relatively thin and suitable to be positioned onto the sample stage of a fluorescence microscope. A fluorescent dye is added to, and evenly distributed within the liquid sample. The dye is selected so that it does not leak into the RBCs. In other words, only the blood plasma is stained with a fluorescent dye. The dye should absorb excitation light within a spectral region where the absorption within the RBCs is weak. The dye also should emit fluorescence light where the absorption within the RBCs is only weak. Since hemoglobin is the dominant absorber in RBCs, the excitation wavelength should preferably be longer than 600 nm. One good candidate dye is TO-PRO-3 (sold, for example, by Molecular Probes, Inc., Eugene, Oreg.), that can be excited within a wavelength range around to 640 nm. Another possible dye would be TO-PRO-5 (also sold by Molecular Probes, Inc.), which also does not penetrate into the RBCs, and can be excited around 750 nm.

Figure 1:
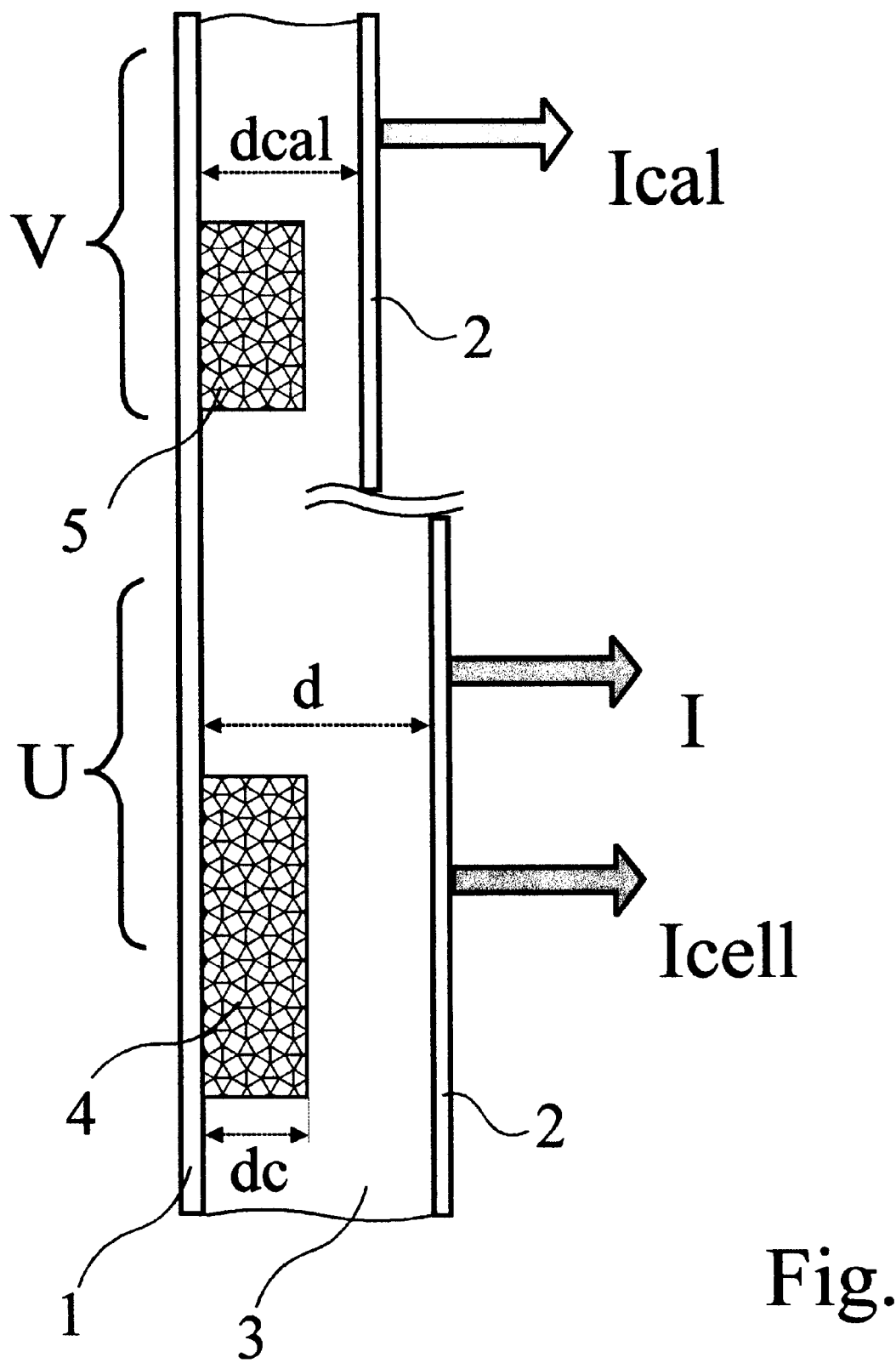
FIG. 1 shows schematically an optical cuvette with a first area of interest, U, having a first thickness d, and with a second area of interest, V, having a second thickness dcal.

FIG. 1 depicts the essential parts of an optical cuvette for microscopic analysis that would be suitable to practice the present invention. The cuvette has a first window (1) and a second window (2), whereby at least one of windows (1) and (2) is transparent. In FIG. 1, window (2) is assumed to be transparent. The cuvette is filled with whole blood (3), comprising RBCs (4) that form Roleaux aggregates. In a real sample, the RBCs will be spread out over the whole available blood volume. In order to make the mathematical modeling more clear, the RBCs (4) in FIG. 1 are shown as collected within a well-defined partial volume of thickness dc. It has to be emphasized that the method according to the present invention can also be modeled in a more complex way with the red cells spread out, but the results would be identical.

In FIG. 1, a first area of interest (U) having a size, A, contains locations with RBCs, and locations without RBCs. The thickness, or optical pathlength, in the first area of interest (U) is represented by the symbol d. A second area of interest (V) having a size Acal=A contains also locations without RBCs, and locations with RBCs (5). The thickness, or optical pathlength, in the second area of interest (V) is represented by the symbol dcal. According to the present invention, thicknesses d and dcal have to be different. The blood sample is illuminated homogeneously with excitation light of a wavelength as discussed above. The fluorescence intensity I in FIG. 1 represents the extrapolated integrated intensity for the whole area of (U) that would be measured if there where no RBCs present. I is determined by measuring fluorescence intensity values in cell-free locations within (U), and then extrapolating to the whole area of (U). The fluorescence intensity Icell in FIG. 1 represents the integrated intensity for the whole area of (U) that is being measured with the RBCs present. The fluorescence intensity Ical in FIG. 1 represents the extrapolated integrated intensity for the whole area of (V) that would be measured if there where no RBCs present.

Figure 2A:
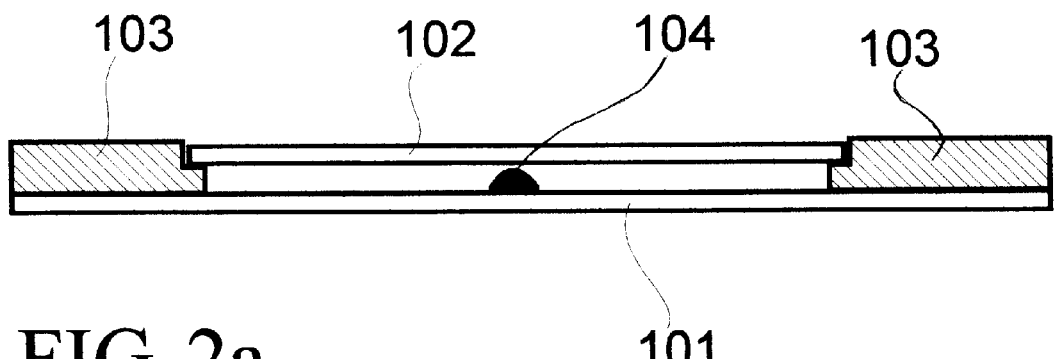
FIGS. 2a, 2b and 2c show an optical cuvette for microscopic analysis with at least two areas of interest having different thicknesses.
Figure 2B:
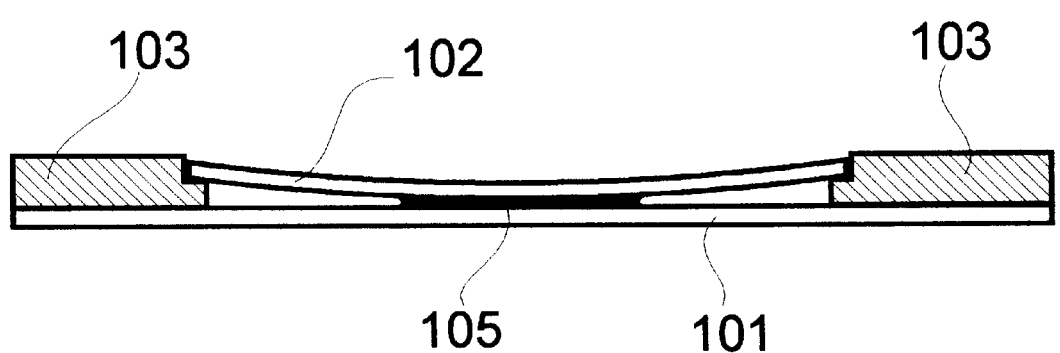
Figure 2C:
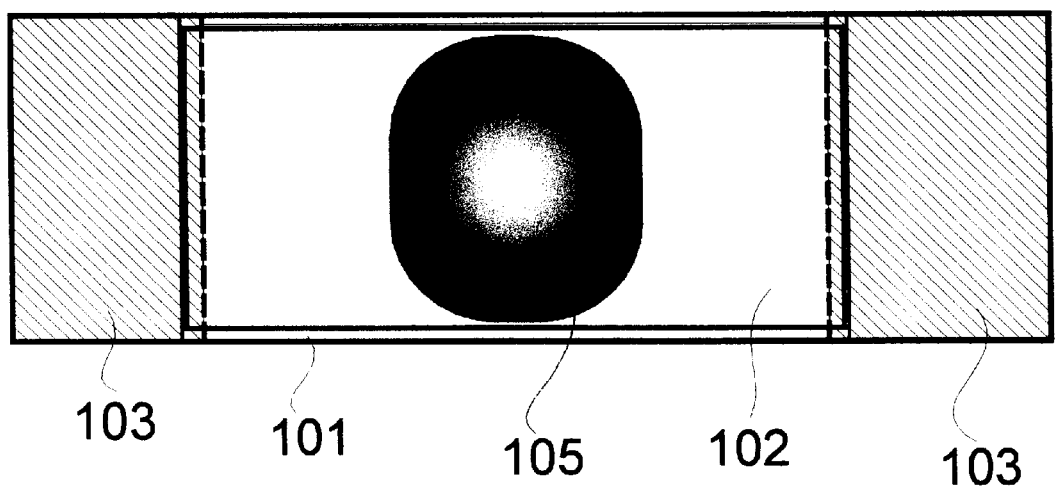

An optical cuvette for microscopic analysis with at least two areas of interest having different thicknesses can be produced easily, e.g. by applying the method as disclosed in U.S. Pat. No. 6,180,314 to Berndt, which is herewith incorporated by reference, and is illustrated in FIGS. 2 a–c. The cuvette is built by using a common microscope slide (101) that carries spacers (103) to hold a flexible cover slip (102). A drop of fluorescently stained whole blood (104) is disposed onto microscope slide (101). By pressing the flexible cover slip (102) downwards until it reaches the drop of blood, capillary forces take over. The blood sample (104) is spreading out, holds coverslip (102) down, and forms a thin blood film (105) having a varying thickness across the area it covers. It is easy to find suitable areas of interest on the blood film.

The method for calibrating a sample analyzer according to the present invention can be summarized in the following nine steps:
1. Measure fluorescence intensity values in cell-free locations within a first area of interest having a size, A, and a first thickness.
2. Extrapolate to the integrated fluorescence intensity, I, from the first area of interest that could be expected under cell-free conditions.
3. Determine the thickness, d, within the first area of interest by utilizing any known method for determining a liquid sample height.
4. Measure the integrated fluorescence intensity, Icell, in said first area of interest, including all cells in this area.
5. Measure fluorescence intensity values in cell-free locations within a second area of interest having a size, Acal=A, and a second thickness.
6. Extrapolate to the integrated fluorescence intensity, Ical, from the second area of interest that could be expected under cell-free conditions.
7. Determine the thickness, dcal, within said second area of interest by utilizing any known method for determining a liquid sample height.
8. Use the quantities I, Ical, d, dcal, and A=Acal to calculate a calibration constant, C, according to the equation $$C = \frac{I - Ical}{(d - dcal) * A}.$$

9. Use the quantities I, Icell, d, C, and A to calculate the HCT value of the sample according to the equation $$HCT = \frac{I - Icell}{C * A * d}.$$

Step 1

The thickness, d, within the first area of interest (U) is considered to be constant since microscopic samples are dealt with here and any given "field of view" under a microscope represents a very small absolute area. For a typical microscope, assuming a 20×objective lens, the field of view has a diameter well below one mm and a typical diameter for U would be around 100 microns. In a sample according to FIGS. 2 a–c, the film extends over a diameter of 20 mm, the minimum film thickness is around 1 micron, and the maximum film thickness is around 30 microns. For a HCT measurement, one would select a first area of interest according to FIG. 1 in a film region, where the thickness is around 20 microns or higher.

This means that within U the thickness will vary by only ±0.7%. The fact that the change in thickness is distributed anti-symmetrically around an average value results in an additional cancellation, so that the overall effect becomes so small that the effect can be neglected.

Step 2

The second step does not require a detailed discussion, since it is well known in the field of image processing how to extrapolate to an integrated intensity from measurements at particular locations. It should be mentioned that the "integrated fluorescence intensity, I", from the first area of interest (U) contains possible contributions from plastic fluorescence and/or from excitation/emission cross-talk.

The integrated fluorescence intensity, I, can be calculated using the equation $$I = I_0 * F * d * A + I_{CT} \qquad (2)$$

wherein $I_0$ is the homogeneous excitation intensity. F represents a constant system transfer function factor involving the fluorescence quantum yield as well as geometrical factors, taking into account what percentage of the emitted photons are directed towards and detected by a photodetector. The quantity A in equation (2) represents the size of the first area of interest. The un-known quantity $I_{CT}$ in (2) represents contributions from excitation/emission cross-talk and/or plastic fluorescence. It would also contain other contributions, e.g. due to stray light a daylight leaking into the instrument, should such effects be present.

Step 3

Any of a series of known methods is used to determine the thickness, d, of the liquid layer within the first area of interest (U). If an exact thickness could be established during the cuvette production, then one would use this number. However, and as mentioned above, tight production tolerances would increase the cost of plastic cuvettes, and it is an objective of the present invention to allow for precise HCT determinations on unprecise cuvettes. In other words, instead of producing millions of extreme precise disposable cuvettes at high cost, one would use cheap cuvettes on a more intelligent instrument.

One known approach for the determination of the thickness, d, in the first area of interest would be to use a confocal microscope. A plot of the number of photons reflected back from a complex cuvette as a function of the focal-plan position along the Z axis exhibits a maximum for every interface between two adjacent media of different index of refraction. The full-width-at-half-maximum (FWHM) along the Z axis is about 2 to 3 microns, and the position of the bell-shaped interface reflex can be determined with sub-micron precision. Therefore, the thickness, d, of the sample layer within the cuvette can be determined from the difference in the Z-positions between the appropriate maxima. As an example, if one assumes a precision of 0.2 microns for locating the two interfaces of interest, then a cuvette thickness of 30 microns could be determined with an error of only 1.3%. There are other methods known that could also be used. One of them is described below in paragraph "Step 8".

Step 4

All that has been said about Step 2 also applies to Step 4, with the exception that here the actual integrated intensity is measured that includes the fluorescence exclusion effect caused by the transparent but non-fluorescent red cells. The integrated intensity, Icell, is given by the equation $$I_{cell} = I_0 * F * (d-dc) * A + I_{CT} \quad (3)$$

where, according to FIG. 1, dc represents the effective thickness of "packed" RBCs. As has been mentioned already, assuming packed RBCs is an allowed simplification. It is important to note that the intensity, Icell, contains the same cross-talk contribution, $I_{CT}$, as the extrapolated intensity I in equation (2). This fact is a consequence of the condition Acal=A, and of the fact that one assumes a homogeneous illumination intensity, $I_0$.

Step 5

Step 5 corresponds to Step 1, but is performed in a second area of interest, (V), having a size Acal=A, but a different thickness.

Step 6

Step 6 corresponds to Step 2, but is performed in said second area of interest (V), having a size, Acal=A. The integrated intensity, Ical, is given by the equation $$I_{cal} = I_0 * F * d_{cal} * A + I_{CT} \quad (4)$$

where dcal is the thickness in this area. It is again important to note that the intensity Icell contains the same cross-talk contribution, $I_{CT}$, as the extrapolated intensity I in equation (2). This fact is a consequence of the condition Acal=A, and of the homogeneous illumination intensity, $I_0$. To achieve a high precision with the method according to the present invention it is of advantage if the thicknesses d and dcal are as different in magnitude as possible.

Step 7

Step 7 corresponds to the procedure described in Step 3, but performed in said second area of interest (V).

Step 8

By subtracting equation (4) from equation (2), an expression for a calibration constant, C, can be obtained which is given by the equation $$C = I_0 * F = \frac{I - Ical}{(d - dcal) * A}. \quad (5)$$

The calibration constant, C, provides information about the change in integrated intensity in a certain area of size A due to a change in thickness. It is important to note that C does not represent a ratio "intensity/volume", but is referring to a differential quantity. Only the differential quantity is independent of contributions from plastic fluorescence and/ or excitation/emission cross-talk. A ratio "intensity/ volume", measured as the integrated intensity emerging from a particular volume (e.g. from one area of known size and thickness) would still be impaired by the above-mentioned contributions.

Step 9

Once a calibration constant, C, has been determined, the HCT value can be calculated by subtracting equation (3) from equation (2), and using the value of C as determined in Step 8 according to equation (5). The equation for the HCT is then $$HCT = \frac{A * d_c}{A * d} = \frac{I - Icell}{C * A * d}. \quad (6)$$

It is of course possible to combine equations (5) and (6) which results in $$HCT = \frac{I - Icell}{I - Ical} * \left[1 - \frac{dcal}{d}\right]. \quad (7)$$

In equation (7), the size, A, of the two areas of interest is not anymore included. The measurements according to the present invention have, however, to be performed under the condition A=Acal to achieve a cancellation of contributions from plastic fluorescence and/or excitation/emission cross-talk.

Figure 3:
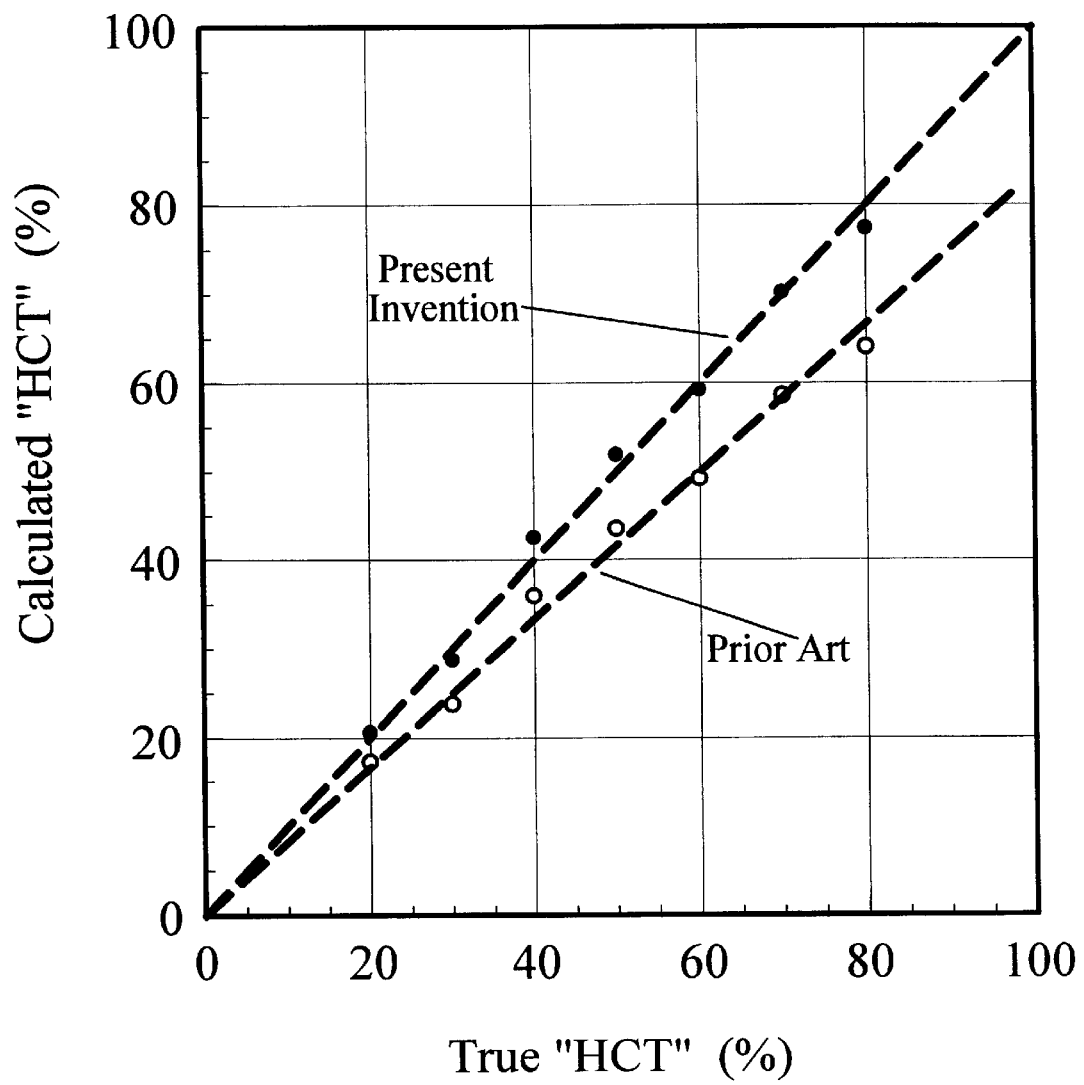
FIG. 3 shows results of HCT measurements according to the present invention, performed on synthetic samples. The second plot illustrates how photon contributions due to plastic disposable fluorescence and/or excitation/emission cross-talk impair the determination of HCT of whole blood in prior art apparatus.
Figure 4:
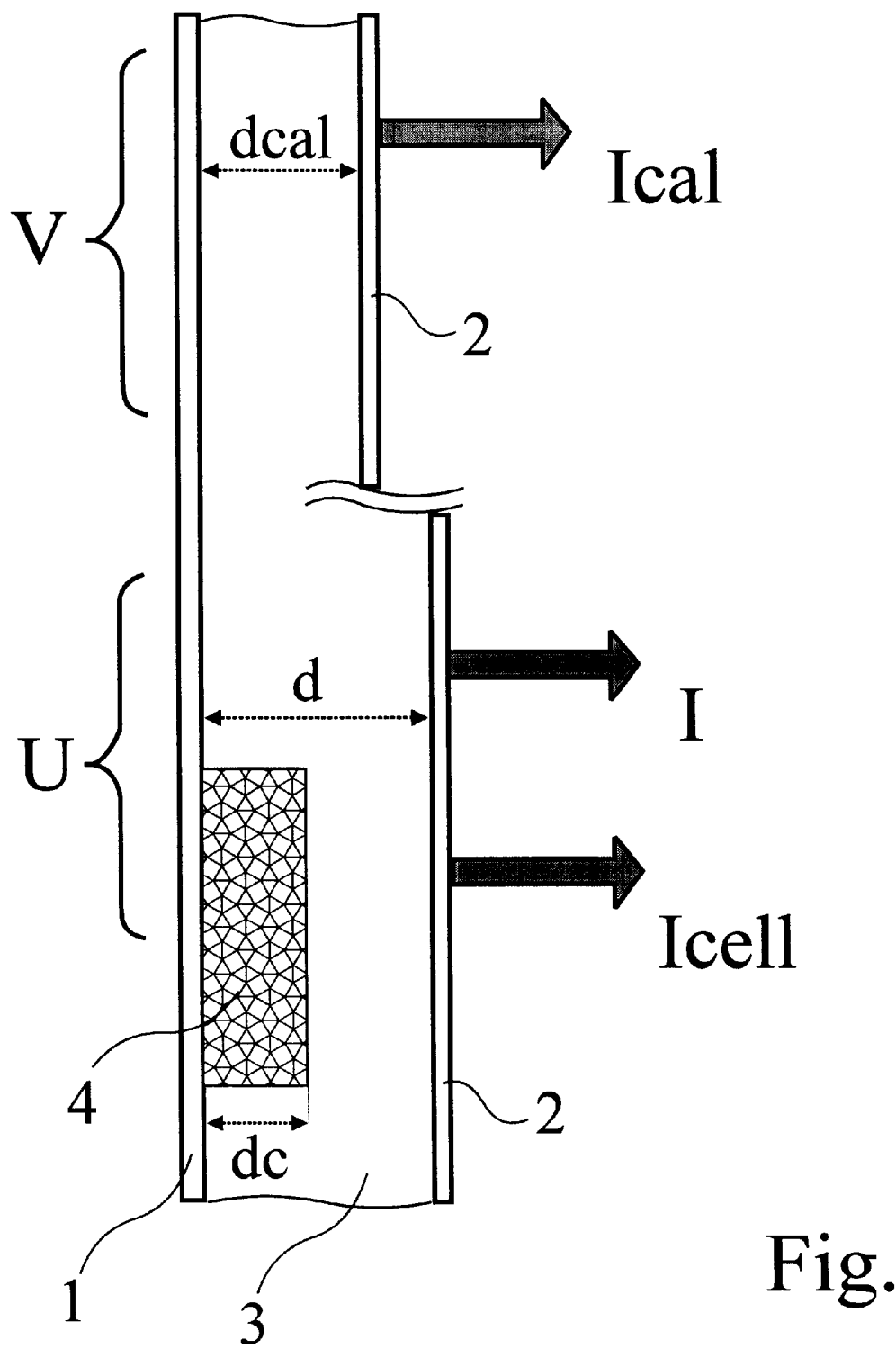
FIG. 4 shows schematically an optical cuvette with a first area of interest, U, having a first thickness d, and with a second cell-free area of interest, V, having a second thickness dcal.

FIG. 3 illustrates preliminary results. Artificial "RBCs" similar to the situation as shown in FIG. 1 have been disposed into a thin optical cuvette according to FIG. 2, having areas of different thicknesses between 1 micron and 100 microns. In this particular experiment, a dichroic filter of low quality has been used, which resulted in an excitation/ emission cross-talk contribution to the overall "fluorescence intensity" by 20%. When a HCT determination according to prior art (i.e., according to equation 1) was performed, the obtained HCT values were too low by 17%, which would not be acceptable for a clinical instrument. A correct HCT value was obtained by using the method according to the present invention (i.e., according to equations (6) and (7)).

The calibration method according to the present invention can also be used to measure the RCV more precisely compared to calibration methods of prior art that suffer from artifacts due to plastic fluorescence and excitation/emission cross-talk. To measure the RCV, one could use an optical cuvette that has an area of large thickness (7–40 microns) and an area of small thickness (2–7 microns). A calibration according to the present invention would be performed in parts of the thick area. In the thin region, monolayers of single isolated RBCs are expected to form. The integrated fluorescence intensity in an area near an RBC is determined, which is given by the equation $$I_P = I_0 * F * d_{ML} * a + I_{CT}' \quad (8)$$

where $d_{ML}$ stands for the thickness in this part of the monolayer region. The quantity a is the size of the selected area of interest. The quantity $I_{CT}'$ represents the usual contributions as mentioned above. The magnitude of $I_{CT}'$ will vary with the size, a, but we expect it to be canceled out anyway by applying the additional steps as described below.

In a next step, the integrated fluorescence intensity, $I_{RBC}$, in an area of identical size, a, that includes said RBC is determined, which is given by the equation $$I_{RBC} = I_0 * F * (d_{ML} - d_{RBC}) * a + I_{CT}' \quad (9)$$

where $d_{RBC}$ stands for the "height" of said RBC. By subtracting equation (9) from equation (8), and selecting the area, a, so that it coincides with the area of the RBC, we obtain for the volume, RCV, of said single cell, the equation $$RCV = \frac{I_P - I_{RBC}}{C}. \quad (10)$$

Equation (10) shows that a difference between two fluorescence intensities is calculated. Consequently, any contributions due to plastic fluorescence and excitation/emission cross-talk would be canceled out. This is particularly important since the true fluorescence from the thin region of the cuvette is extremely weak due to the small thickness. Therefore, such contributions can represent a substantial percentage of the measured intensity. In some cases, they can be the dominant part of the measured intensity.

So far, we have assumed that the RBC has a cylindrical shape. It can be shown that the shape of the RBC can be irregular and that the Z-position of the cell within the cuvette has no impact on the calculated cell volume. The integrated intensity, $I_{RBC}$, given in equation (9) can also be written for a spatially varying cell height, $h_{RBC}(x,h)$, by the following equation:

$$I_{RBC} = I_0 * F * \int [d_{ML} - h_{RBC}(\xi,\eta)]d\xi d\eta + I_{CT}. \quad (11)$$

In equation (11), the quantities x and h represent the independent X- and Y-variables within the RBC. In practice, the required integration is easily performed by adding the pixel intensities within the area, a. The same applies to the HCT determination described above.

Figure 5:
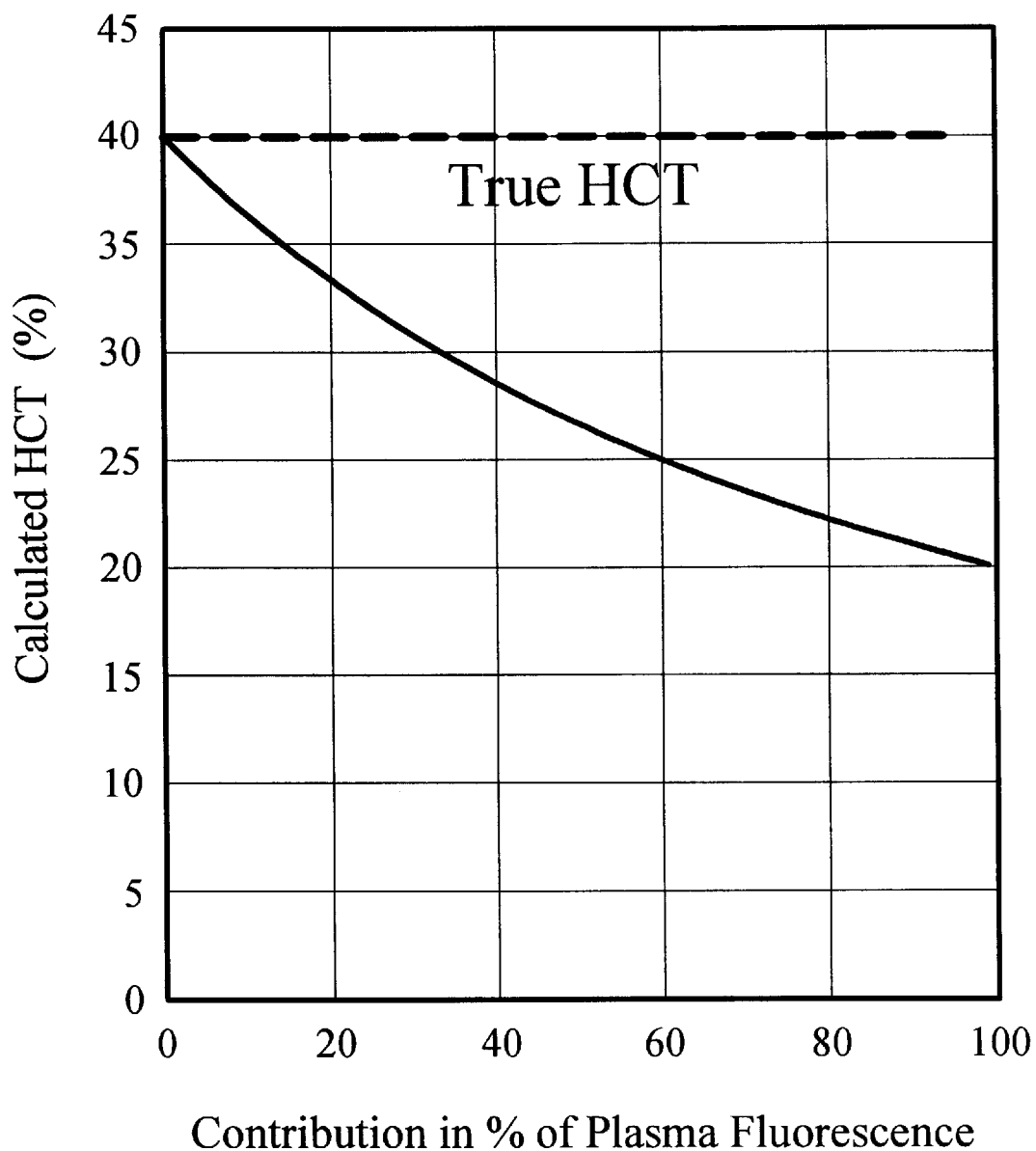
FIG. 5 shows a plot illustrating how an increasing contribution from plastic fluorescence and/or excitation/ emission cross-talk to the plasma fluorescence can impair the calculated HCT value.

Finally, it is important to note that in the calibration method according to the current invention, the second area of interest, (V), does not need to contain any RBCs. Such a situation is illustrated in FIG. 5. As has been mentioned already, the precision of the calibration according to the present invention is particularly high, if the difference in thickness between the first and second area of interest is as large as possible. In the first area of interest, one wants RBCs in Roleaux formation. Therefore, this area may have a thickness around 30 microns. This leads naturally to a small thickness for the second area of interest. A small thickness usually results in more cell-free areas.

FIG. 5 shows another plot illustrating again how an increasing contribution from plastic fluorescence and/or excitation/emission cross-talk to the plasma fluorescence can impair the calculated HCT value, if prior art methods are applied. Only for cuvettes that exhibit a very low fluorescence, and for high-quality dichroic filter units, the calculated HCT value will be close to the true value. In contrast, the method according to the present invention allows to use fluorescent plastic materials for the cuvettes, and to use lower-grade dichroic filters, and still obtain exact HCT values.

I claim:

1. A method for calibrating a blood analyzer held within an optical scanning instrument, in order to determine the hematocrit (HCT) value of a sample of blood, said method comprising:
   a) providing a chamber for receiving a blood sample, in said blood analyzer;
   b) depositing the sample into said chamber wherein said sample contains a fluorescent dye;
   c) illuminating said sample with excitation light;
   d) scanning the sample with said instrument to detect the fluorescence from said sample;
   e) measuring fluorescence intensity values in cell-free locations within a first area of interest having a size, A, and a first thickness;
   f) extrapolating to an integrated fluorescence intensity, I, from the first area of interest that could be expected under cell-free conditions;
   g) determining the first thickness, d, within the first area of interest by utilizing any known method for determining a liquid sample height;
   h) measuring an integrated fluorescence intensity, Icell, in said first area of interest, including all cells in this area;
   i) measuring fluorescence intensity values in cell-free locations within a second area of interest having a size, Acal=A, and a second thickness;
   j) extrapolating to an integrated fluorescence intensity, Ical, from the second area of interest that could be expected under cell-free conditions;
   k) determining the second thickness, dcal, within said second area of interest by utilizing any known method for determining a liquid sample height;
   l) using the quantities I, Icell, Ical, d, dcal, to calculate the HCT value of the sample by means of an equation that contains pairs of differences of integrated fluorescence intensities; and
   m) obtaining the HCT value of the sampler with said calibrated blood analyzer.

2. The method of claim 1 wherein the HCT value of the sample is calculated according to the equation $$HCT = \frac{I - Icell}{I - Ical} * \left(1 - \frac{dcal}{d}\right).$$

3. The method of claim 1 wherein
   a) first a calibration constant, C, is determined according to the equation $$C = \frac{I - Ical}{(d - dcal) * A}$$

and secondly
   b) the HCT value of the sample is calculated according to the equation $$HCT = \frac{I - Icell}{C * A * d}.$$

4. The method of claim 1 wherein said sample is whole blood.

5. The method of claim 1 wherein said chamber is an optical cuvette.

6. The method of claim 1 wherein said optical scanning instrument is a fluorescence microscope.

7. The method of claim 1 wherein said optical scanning instrument is equipped with a photodetector.

8. The method of claim 1 wherein said optical scanning instrument is equipped with an imaging photodetector.

9. The method of claim 1 wherein said fluorescent dye within said sample is selected so that it does not penetrate into cells.

10. The method of claim 1 wherein said fluorescent dye within said sample is selected so that it absorbs excitation light within a spectral region where absorption within cells in the sample is only weak.

11. The method of claim 1 wherein said fluorescent dye is illuminated with excitation light having a wavelength that is longer than 600 nm.

12. The method of claim 1 wherein said fluorescent dye within said sample is selected so that it can emit fluorescence light within a spectral region where absorption within cells in the sample is only weak.

13. A method for calibrating a blood analyzer held within an optical scanning instrument, in order to determine the volume of single red cells (RCV) in a sample of blood, said method comprising:
   a) providing a chamber for receiving a blood sample, in said blood analyzer;
   b) depositing the sample into said chamber wherein said sample contains a fluorescent dye;
   c) illuminating said sample with excitation light;
   d) scanning the sample with said instrument to detect the fluorescence from said sample;
   e) measuring fluorescence intensity values in cell-free locations within a first area of interest having a size, A, and a first thickness;
   f) extrapolating to an integrated fluorescence intensity, I, from the first area of interest that could be expected under cell-free conditions;
   g) determining the first thickness, d, within the first area of interest by utilizing any known method for determining a liquid sample height;
   h) measuring fluorescence intensity values in cell-free locations within a second area of interest having a size, Acal=A, and a second thickness;
   i) extrapolating to an integrated fluorescence intensity, Ical, from the second area of interest that could be expected under cell-free conditions;
   j) determining the second thickness, dcal, within said second area of interest by utilizing any known method for determining a liquid sample height;
   k) using the quantities I, Ical, d, and dcal, to calculate a calibration constant, C;
   l) measuring an integrated fluorescence intensity, $I_{RBC}$, in a third area of interest within a monolayer region that is totally occupied by a single red cell of area, a;
   m) measuring fluorescence intensity values in cell-free locations within a fourth area of interest close to said single red cell and having the area, a,
   n) extrapolating to an integrated fluorescence intensity, $I_P$, from the fourth area of interest that could be expected under cell-free conditions;
   o) using the values C, $I_P$, and $I_{RBC}$ to calculate the RCV value of said single red cell by means of an equation that contains pairs of differences of integrated fluorescence intensities; and
   p) obtaining the RCV value for said single red cell with said calibrated blood analyzer.

14. The method of claim 13 wherein the calibration value, C, is calculated according to the equation $$C = \frac{I - Ical}{(d - dcal) * A}.$$

15. The method of claim 13 wherein the RCV value of the single red cell, is calculated according to the equation $$RCV = \frac{I_P - I_{RBC}}{C}.$$

16. The method of claim 13 wherein said sample is whole blood.

17. The method of claim 13 wherein said chamber is an optical cuvette.

18. The method of claim 13 wherein said optical scanning instrument is a fluorescence microscope.

19. The method of claim 13 wherein said optical scanning instrument is equipped with a photodetector.

20. The method of claim 13 wherein said optical scanning instrument is equipped with an imaging photodetector.

21. The method of claim 13 wherein said fluorescent dye within said sample is selected so that it does not penetrate into cells.

22. The method of claim 13 wherein said fluorescent dye within said sample is selected so that it absorbs excitation light within a spectral region where absorption within cells in the sample is only weak.

23. The method of claim 13 wherein said fluorescent dye is illuminated with excitation light having a wavelength that is longer than 600 nm.

24. The method of claim 13 wherein said fluorescent dye within said sample is selected so that it can emit fluorescence light within a spectral region where absorption within cells in the sample is only weak.

* * * * *